United States Patent [19]

Zanetti

[11] Patent Number: 4,883,460
[45] Date of Patent: Nov. 28, 1989

[54] TECHNIQUE FOR REMOVING DEPOSITS FROM BODY VESSELS

[76] Inventor: Paul H. Zanetti, 5226 St. Andrews, Corpus Christi, Tex. 78413

[21] Appl. No.: 185,435

[22] Filed: Apr. 25, 1988

[51] Int. Cl.$^4$ .............................................. A61B 17/20
[52] U.S. Cl. ...................................... 604/22; 128/305
[58] Field of Search .................. 604/22; 128/305, 311, 128/328, 91 A

[56] References Cited

U.S. PATENT DOCUMENTS

| | | | |
|---|---|---|---|
| 3,352,303 | 11/1967 | Delaney | 128/24 A |
| 3,495,590 | 2/1970 | Zeiller | 128/91 A |
| 4,445,509 | 5/1984 | Auth | 128/305 |
| 4,728,319 | 3/1988 | Masch | 604/22 |
| 4,732,154 | 3/1988 | Shiber | 128/305 |
| 4,749,376 | 6/1988 | Kensey et al. | 604/22 |
| 4,772,258 | 9/1988 | Marangoni et al. | 604/22 |
| 4,784,636 | 11/1988 | Rydell | 128/305 |
| 4,808,153 | 2/1989 | Parisi | 604/22 |

*Primary Examiner*—Dalton L. Truluck
*Attorney, Agent, or Firm*—G. Turner Moller

[57] ABSTRACT

A technique for removing plaque from blood vessel includes passing a wire saw-catheter assembly through an artery to a location adjacent an area of plaque buildup. The wire saw is then moved out of the end of the catheter into engagement with the plaque buildup. The wire saw is reciprocated through a stroke of 0.01-4 millimeters at a rate of between 3,000-30,000 cycles per second. In one embodiment, the wire saw is straight while a second embodiment of the wire saw includes a a curved end. In both embodiments, a triangularly shaped cutting element is helically wound about the tube end. The cutting element reciprocates against and comminutes the relatively hard plaque without damaging the relatively soft blood vessel. The debris produced by the action of the wire saw is removed by a variety of techniques causing liquid flow back through the catheter including: (1) delivering a quantity of liquid through the end of the cutting tool, (2) applying suction to the catheter, and (3) blocking flow in the artery at an effective location. The technique also disintegrates and removes other hard, relatively immobile deposits from ducts, such as gall or kidney stones.

11 Claims, 3 Drawing Sheets

TECHNIQUE FOR REMOVING DEPOSITS FROM BODY VESSELS

This invention relates to a technique for removing relatively hard deposits from body vessels, such as arteriosclerotic deposits from the inside of blood vessels.

The most common disease of human arteries is the accumulation of a relatively hard material known as arteriosclerotic plaque. These accumulations slowly close the artery lumen until the quantity of blood passing through the artery is insufficient to sustain the body part to which the artery leads. All sorts of complications can occur, depending on where the involved artery leads. Compromise of the coronary arteries can lead to death of part of the heart muscle because of oxygen deprivation Coronary infarction or heart attack is the result. Reduced blood flow in the carotid artery leading to the brain leads to transient ischemic attach or stroke. Blockage or substantially reduced blood flow in the other arteries leads to impairment of the limbs or other organs.

At present there are a number of accepted techniques for treating this condition such as: (1) endarterectomy which is surgically opening the artery under direct vision and dissecting out the plaque; (2) replacement which is surgically removing the impaired artery and replacing it with either a tube of artificial removal or another blood vessel, usually a vein; (3) bypass which is attaching a length of a tube of artificial material or another blood vessel, usually a vein, to the involved artery both proximal and distal to the involved segment to "bypass" this segment. Because of the extensiveness, cost and risk of these procedures, an extensive effort is being made to find a simpler, less expensive, less risky procedure This search has led to a technique known as balloon angioplasty in which a catheter is passed into the afflicted artery and a balloon is expanded in the area of narrowing to enlarge the opening therethrough Balloon angioplasty has a number of drawbacks: (1) it is limited to the treatment of short stenotic segments, not long areas of narrowing; (2) it tends to be limited to larger arteries; (3) it works by fracturing the plaque which can cause emboli and also results in a rough thrombogenic surface subject to further emboli formation; and (4) in about a third of the cases it doesn't work because the affected artery returns to substantially its original condition in a few months. Despite these drawbacks, balloon angioplasty is a very common procedure because the alternative surgery is so much less appealing.

There is presently a great deal of effort being spent to build and learn how to operate a laser device which can be inserted through a catheter into an afflicted artery to remove a significant portion of the accumulated plaque. See U.S Pat. No. 4,207,874. The main problem is that lasers operate by vaporizing the plaque and there is a tendency to burn a hole in or thermally damage the afflicted artery. The latest known concept in this area is to use the laser technique immediately after balloon angioplasty in an effort to smooth out the interior vessel wall— there evidently being some evidence to show that the more ragged the wall after balloon angioplasty, the more likely that premature reclosure occurs.

Disclosures of interest relative to this invention are found in U.S. Pat. Nos. 2,230,997; 2,407,690; 2,944,552; 2,955,592; 3,074,396; 3,352,303; 3,358,677; 3,433,226; 3,448,741; 3,525,339; 3,565,062; 3,683,891; 3,730,185; 3,749,085; 3,830,340; 4,020,847; 4,030,503; 4,203,444; 4,207,874; 4,273,128; 4,445,509; 4,519,344; 4,552,554, 4,553,534; 4,574,781; 4,589,412; 4,646,736; 4,653,496; 4,679,557; and 4,696,667 and France Pat. Nos. 540,428 and 991,494.

The problem is to remove a significant portion of the plaque from the vessel while doing as little damage to the vessel wall as practicable. The approach of this invention is to take advantage of the difference in hardness between the relatively hard inflexible plaque and the relatively soft pliable vessel wall. Relying on this difference underlies the approach shown in U.S. Pat. No. 4,445,509 in which a mechanical cutter is rotated inside the vessel wall to reduce the plaque to small particles which are withdrawn or flushed out of the vessel. While development of this approach appears to be continuing, it has not yet achieved any degree of acceptance.

In any technique of this general type, the physician first locates the area or areas of partial blockage in any conventional fashion, usually by an X-ray technique in which a radiopaque dye has been injected into the blood vessel and periodic X-ray exposures taken of the afflicted vessel. In the technique of this invention, an "access" catheter is inserted through the skin into the arterial system or directly into a surgically exposed artery, and advanced under X-ray guidance into the target artery until the end of the access catheter is near the area of partial blockage. A wire saw is inserted through the access catheter and advanced through or into the area of partial blockage. It is then rapidly reciprocated through a rather short stroke The combination of rapid reciprocation and short stroke of the wire saw acts to disintegrate the relatively hard plaque without damage to the blood vessel.

It will be apparent, upon reflection, that this technique makes perfect sense because the principle is accepted in other situations. For example, one type of cast cutter includes a circular blade that is rapidly oscillated through a very small arc. A typical cast cutter oscillates at 17,000 cycles per minute with no load and about 13,000 cycles per second while cutting. The stroke of this cast cutter is about $\frac{1}{8}''\pm 1/64''$. The blade effectively cuts the rigid cast material without damaging the skin beneath the cast because human skin is much more resilient.

The success of the wire saw of this invention in disintegrating the hard plaque creates its own problem—the generation of a large amount of debris. Manifestly, all or a large part of the debris must be removed from the patient. This is accomplished by several techniques which are presently within the skill of those adept in vascular procedures. In situations where the physician intends to extend the wire saw in a direction leading away from the heart, forward blood flow through the involved or target artery is stopped by either the inflation of an outer balloon at the distal end of the access catheter or, if the artery has been surgically exposed, by a temporary clamp applied upstream from where the catheter is inserted. Most of the blood then entering the affected artery will come from collaterals, i.e. smaller arteries which bypass the temporarily blocked artery. Therefore, any blood which comes back through the catheter will be flowing backwards or so called "back bleeding". By placing suction on the catheter, this blood flow will be augmented and tend to wash any debris back through the catheter and out of the patient. Furthermore, the wire saw preferably comprises an elongate tubular member leading through the catheter to the exterior of the patient. A liquid solution may be injected through the saw to the free or distill end of the wire saw to flush the debris through the blood vessel toward the opening through which the catheter extends. In those situations where the wire saw-catheter arrangement is inserted into the body toward the heart, debris may be removed from the artery merely by allowing the patient to bleed through the catheter opening.

Full scale tests conducted on obstructed human cadaver arteries reveals almost complete reduction of plaque without apparent significant deleterious affect on the softer tissue of the blood vessel. Preliminary investigations toward removing gall or kidney stones lodged in gall or kidney ducts appears promising.

It is accordingly an object of this invention to provide a technique for removing plaque and other relatively hard obstructions from their respective vessels without substantially damaging the vessel wall.

Another object of this invention is to provide a technically simple, relatively quick, relatively safe technique for removing atherosclerotic plaque from blood vessels.

These and other objects of this invention will become more fully apparent as this description proceeds, reference being made to the accompanying drawings and appended claims, to which reference is made for a more complete description of this invention.

IN THE DRAWINGS

Figure 1:
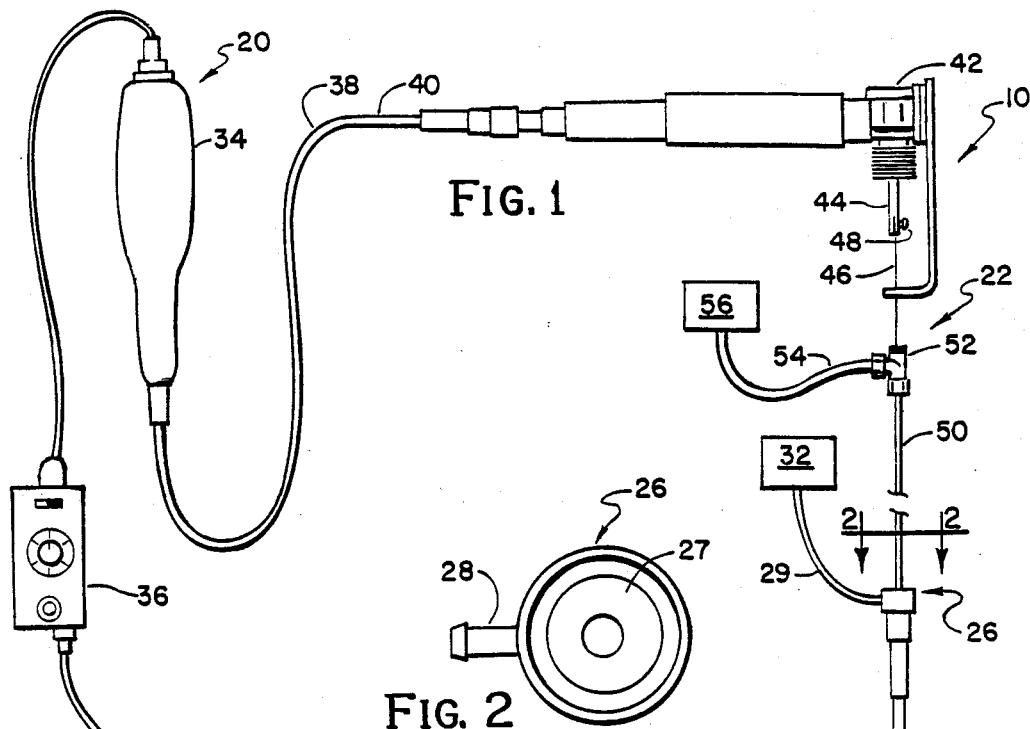
FIG. 1 is an overall view of the device of this invention in the process of being used.
Figure 2:
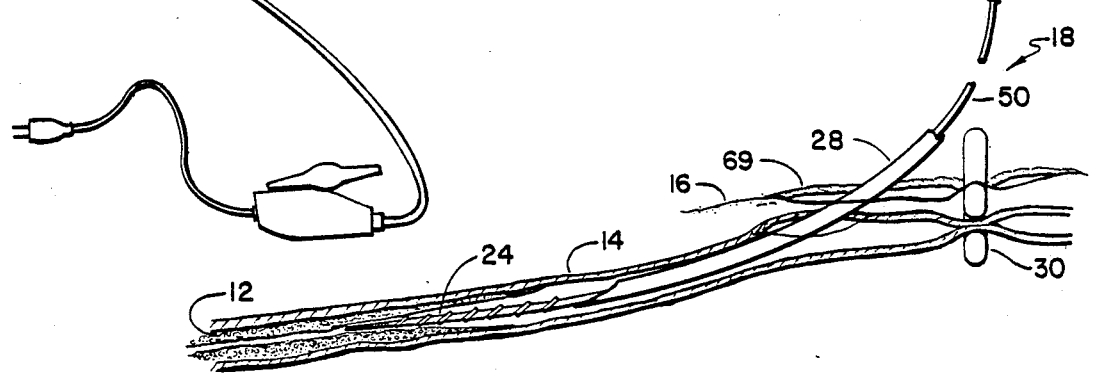
FIG. 2 is a cross-sectional view of the apparatus of FIG. 1, taken substantially along line 2—2, as viewed in the direction indicated by the arrows.

Referring to FIGS. 1-4, an apparatus 10 of this invention is being used to remove an accumulation of atherosclerotic plaque 12 from an artery 14 of a patient. Access to the artery 14 is gained through a small incision in the patient's skin 16 or by using a longer incision and exposing the artery surgically as is well known to those adept in vascular procedures. The apparatus 10 comprises, as major components, a catheter 18 extending from outside the patient to a position in the blood vessel 14 to be treated, a power source 20 for reciprocating a flexible drive element 22, and a cutting tool 24 for comminuting the hard plaque accumulation 12 inside the artery 14.

The catheter 16 may be a simple sheath or access catheter of the type shown in FIG. 1 which includes a seal type fitting 26 having a rubber diaphragm 27 for purposes more fully explained hereinafter. The catheter 16 also includes an elongate tube 28 connected at one end thereof to the fitting 26 and extending into the patient's artery 14.

As will become more fully apparent hereinafter, one of the important functions of the apparatus 10 is to allow the physician to remove the debris generated by comminuting the plaque. In some situations, the catheter tube 28 merely extends into the artery 14 and the artery 14 is closed by a clamp 30. This type situation may occur when working on an artery in the patient's leg and the flexible drive element 22 is going to be passed downward through the artery 14 toward the patient's foot. Irrigation of the artery 14 may be easily accomplished merely by connecting a tube 29 leading from the fitting 26 and communicating with the tube 28 to a source 32 of vacuum and passing a sterile solution downwardly through the flexible drive element 22 as will be explained more fully hereinafter. Other situations will be described momentarily.

The power source 20 may be of any suitable type capable of generating very rapid oscillations of the flexible drive element 22 through a fairly short stroke. The goal of this procedure is to cut, abrade or comminute the plaque 12 into objects of small size that can be removed from the patient's body through the catheter 16 without unduly damaging the patient's artery 14. To this end, the oscillations of the flexible drive element should be quite rapid and short, on the same order of magnitude as that found in cast cutters. Investigations indicate there is a fairly wide range of oscillations and a fairly narrow range of stroke that successfully reduce the plaque 12 without damage to the artery 14. It appears that plaque can be successfully removed by oscillating the cutting element on the order of 3,000-30,000 cycles per minute and moving it through a stroke on the order of 0.01-5 millimeters. It is clear that some shortening or attenuation of the stroke of the cutting element 22 occurs as the flexible drive shaft becomes longer and convoluted. Thus, the measured stroke at the fitting 26 is probably not exactly the same as the actual stroke of the cutting tool 24. They are, however, close. Strokes of 0.01 millimeters or less at the fitting 26 are likely completely attenuated at the end of the cutting tool 24. Strokes much longer than about 5 millimeters are probably so large that human tissue is cut because the elasticity of human tissue is not sufficient.

To these ends, the power source 20 includes an electrically driven rotary device 34 having a motor speed controller 36 in circuit therewith for rapidly rotating a cable 38 housed inside a resilient sheath 40. The cable 38 is connected to a rotary-to-reciprocating motion conversion device 42 having a reciprocating output 44. In a prototype of the apparatus 10, the rotary device 34, cable 38 and sheath 40 are provided by a Dremel Moto-Tool, Model 275, single speed, electrically driven tool having a rated speed of 28,000 rpm, the speed controller 36 is a Dremel Motor Speed Controller and the motion conversion device 42 is a customized model airplane motor in which the crankshaft is driven by the cable 38 and the piston is used as the output 44. No model airplane motor was found having a stroke in the range desired and two were customized, one having a stroke of 2.6 mm and one having a stroke of 3.6 mm. Both versions of the apparatus 10 appear to function satisfactorily.

The output 44 is connected to the flexible drive member 22 in any suitable fashion, as by inserting a relatively rigid end 46 of the drive member 22 into a set screw arrangement 48 carried by the end of the output 44. The flexible drive member 22 is designed to pass an irrigating liquid therethrough to assist in the removal of debris from the artery 14 during and after comminution of the plaque accumulation 12. To this end, the drive member 22 includes an elongate tubular section 50 connected to the end 46. The rigid drive end 46 passes through a perforate resilient diaphragm (not shown), similar to the diaphragm 27, provided by an ell 52 and is generally coaxial with the drive tube 50. The ell 52 is connected through a flexible conduit 54 to a source 56 of sterile liquid for irrigating the artery 14. As is apparent from FIGS. 1 and 2, the drive tube 50 passes through the sealing rubber diaphragm 27 and catheter tube 28 into the artery 14.

Figure 3:
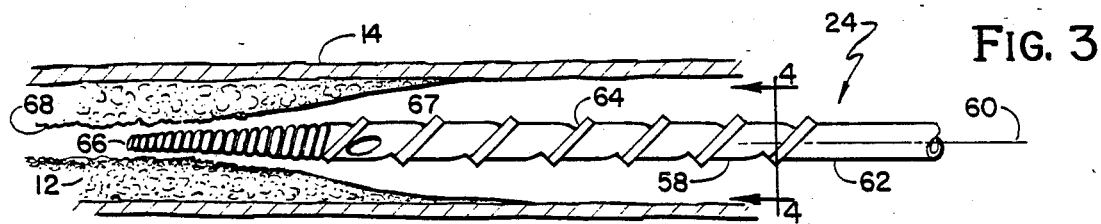
FIG. 3 is an enlarged view of the cutting implement of this invention inside an affected artery in preparation for removing a plaque accumulation.
Figure 4:
FIG. 4 is an enlarged cross-sectional view of the implement FIG. 3 taken substantially along line 4—4, as viewed in the direction indicated by the arrows.

Attached to the end of the drive tube 550 is a cutting tool or wire saw 24 of this invention, shown best in FIGS. 3 and 4, comprising a central tubular support 58 having an axis 60 and providing an exterior surface 62 extending along the axis 60 and providing a helically wound ridge like cutting element 64 extending along the exterior surface 62. The cutting tool 24 is somewhat more rigid than the flexible drive member 24. To facilitate feeding the cutting tool 24 through the artery 14 and plaque accumulation, a flexible guide wire 66 is attached to the forward or distill end of the cutting tool 24. The guide wire 66 is more flexible than the tubular support 58 of the cutting tool 24 and comprises a tightly wound spring which may be spiral or tapered, as shown, or of constant diameter. A very early prototype of the cutting tool 24 of this invention comprised a wire saw available from X-Acto, a subsidiary of Hunt Manufacturing Company of Philadelphia, Pennsylvania. The cutting element of the X-Acto device was excellent, but the commercially available wire saw did not have a tubular center. The cutting tool 24 of the latest prototype is made by machining a stainless steel tube with a grooved grinding wheel to provide the helically wrapped ridge like cutting element 64 which is generally triangularly shaped in cross-section as shown best in FIG. 4. Irrigation liquid delivered from the source 56 through the tube 50 exits through the end of the tubular support 58 or through one of a plurality of transverse exit openings 67.

As will be evident to those skilled in the art, the procedure of this invention is preceded by tests and X-ray angiograms to locate the blockage in the artery 14. The illustration of FIG. 1 assumes that the location of the plaque accumulation 12 is not far from the point of entry into the artery 14. Thus, the drive element 22 and catheter tube 28 are fairly short. The catheter tube 28 is inserted into the artery and movement of the catheter tube 28 is monitored by the use of periodic X-ray angiograms. When the end of the tube 28 approaches the plaque 12, movement of the catheter 16 is stopped and the drive member 22 is axially advanced through the fitting 26 so the cutting tool 24 and guide wire 66 exit from the end of the tube 28 at a location near the plaque 12 and preferably inside the area of reduced artery cross section as suggested in FIGS. 2 and 3.

The power source 20 is then energized to reciprocate the drive member 22 and the cutting tool 24. Because the leader 66 is relatively resilient, it tends to follow the passage 68 through the plaque accumulation 12. As the cutting tool 24 reciprocates through the small passage 68, the cutting element 64 on the exterior surface 62 of the cutting tool 24 engages the relatively rigid plaque thereby cutting some of it loose from the larger plaque accumulation 12. With the artery 14 sealed by the clamp 30, a slight vacuum is drawn on the catheter tube 28 by the vacuum source 32 and a sterile liquid is passed from the source 56 through the drive member 24 to exit near the end of the tool 24. Because of the pressure relationship, debris generated by the cutting tool 24 flows backwardly toward the access fitting 26 and exits from the patient's body through the incision 69 in the skin 16.

The flexible drive member 22 and cutting tool 24 are advanced through the passage 68 of reduced cross section and the plaque accumulation 12 under the control of the physician and monitored by X-ray angiograms. When the area of plaque accumulation is opened up, the cutting tool 24 is withdrawn back into the catheter tube 28. Before removing the catheter tube 28 from the artery 14, an X-ray angiogram is taken to make sure the artery is opened up. The artery 14 is sewn up and the incision 69 closed in a conventional manner. It will be seen that the plaque accumulation 12 is reduced in a simple expeditious manner with very little risk of significantly damaging the artery 14.

Figure 5:
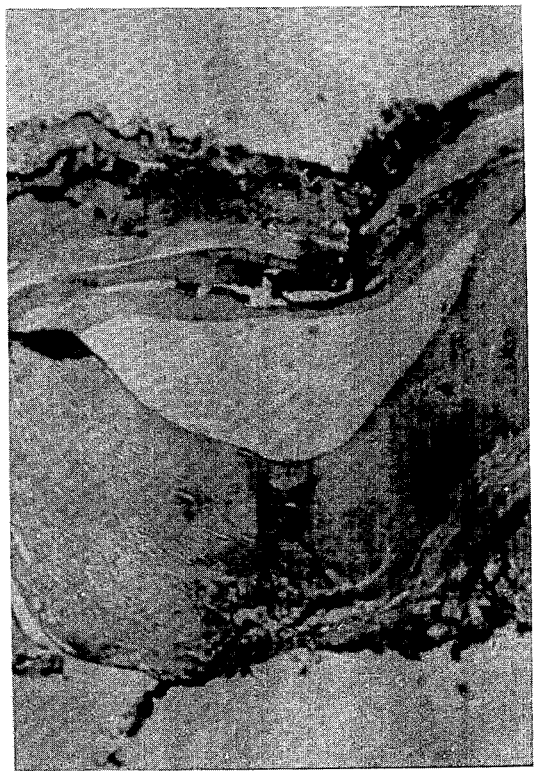
FIG. 5 is a photograph of a partially blocked human cadaver artery.
Figure 6:
FIG. 6 is a photograph of the cadaver artery of FIG. 5 after treatment by the technique of this invention.

FIG. 5 is a cross-sectional view of a partially blocked human cadaver artery showing a substantial plaque accumulation. The corresponding X-ray angiogram of the artery of FIG. 5 shows an area of substantially reduced blood flow path, as might be expected. The technique of this invention was used to remove a significant part of the plaque accumulation as is evidenced by the photograph of FIG. 6 showing the same artery. The corresponding X-ray angiogram shows significantly increased flow capacity in the artery. An important and interesting feature of the technique of this invention is that the inner wall of the artery appears smooth and relatively even.

Because the cutting done by the tool 24 is performed by the cutting element 64 on the elongate exterior surface 62, it would seem that the passage 68 could not be widened substantially because the cutting tool 24 is only reciprocated and the tool 24 should follow the trace of the axis 60. The available evidence suggests, however, that there is some lateral movement or whip of the straight cutting tool 24 because it is effective to create a passage through the plaque accumulation 12 larger than the diameter of the cutting element.

Figure 7:
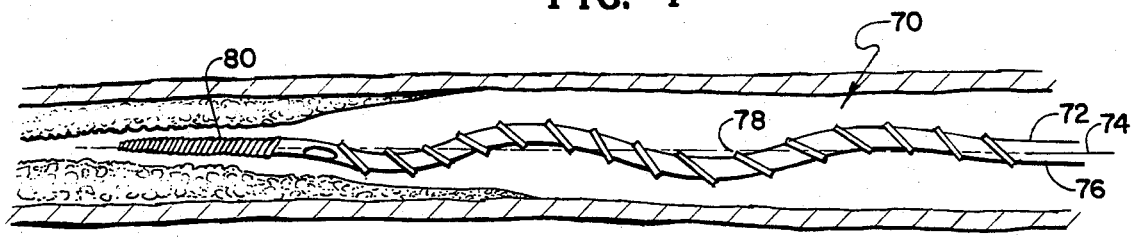
FIG. 7 is a view, similar to FIG. 3, of another embodiment of the cutting tool of this invention.
Figure 8:
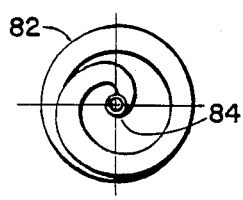
FIG. 8 is a side elevational view of still another embodiment of the cutting tool of this invention.

In much larger arteries, the cutting tool 70 shown in FIG. 7 is preferred. The cutting tool 70 comprises a central tubular support 72 having an axis 74 and providing an exterior surface 76 extending along the axis 74 and providing a helically wound ridge like cutting element 78 extending along the exterior surface 62. The cutting tool 70 is somewhat more rigid than the flexible drive member 24. To facilitate feeding the cutting tool 70 through the artery and plaque accumulation, a guide wire 80 is attached to the forward or distil end of the cutting tool 70. The guide wire 80 is more flexible than the tubular support 72 and comprises a tightly wound helical spring. In order to cut a larger hole in the plaque accumulation, the distil end of the cutting tool 70 is curved and meanders about the axis 74 in a more-or-less regular fashion. The cutting tool 74 of FIG. 7 makes a helical curve about the axis 74. The cutting tool 82 of FIG. 8 makes a spiral curve about its axis 84.

Figure 9:
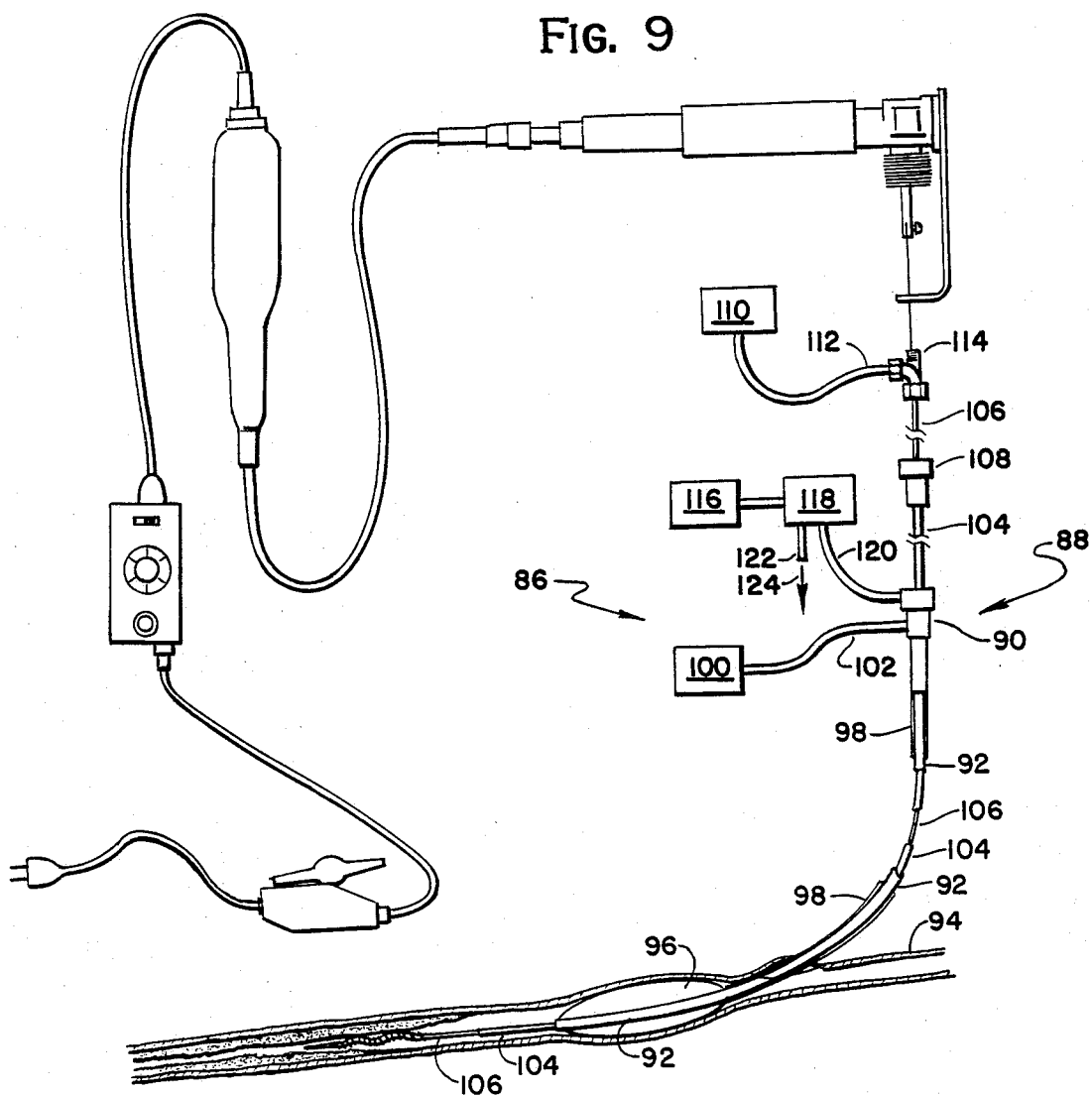
FIG. 9 is a view of another embodiment of this invention.

The illustration of FIG. 1 represents a situation where the plaque accumulation 12 is relatively near the incision 68 and the distance the cutting tool 24 is passed through the artery is relatively short. There are common situations where it is necessary or desirable to reduce a plaque accumulation that is a considerable distance from a convenient incision site. Referring to FIG. 9, a more complicated catheter arrangement 86 is provided to resolve this problem and others, as will be apparent as this description proceeds.

The catheter 86 comprises an access type catheter 88 having a fitting 90 and a tube 92 extending from the fitting 90 into the artery 94 of the patient. An expandable balloon 96 on the exterior of the tube 92 is inflatable through a tube 98 leading to the fitting 90 and connected to a source of fluid pressure 100 through a tube 102. With the catheter tube 92 and balloon 96 in place and expanded, a second catheter 104 is passed through the access fitting 90 and artery 94 to a location adjacent the plaque accumulation. Preferably, the flexible drive member 106 and cutting tool is located inside the catheter 104 as it passes through the artery 94 to the site where plaque is to be comminuted. When the end of the catheter 104 reaches the site, the flexible drive member 106 is advanced through the fitting 108 to advance the cutting tool to adjacent the plaque to be removed. Shortly before reciprocation of the cutting tool begins, the artery 94 is irrigated by delivering a sterile solution from the source 110, tube 112 and ell 114 through the flexible drive member 104 to the end of the cutting tool and drawing a vacuum through the catheter 86 by connecting the same to a source of vacuum 116 acting on a trap 118 connected to the fitting 90 through a tube 120. The solution delivered to the end of the cutting tool flows back toward the balloon 96, through the tube 92, fitting 90, tube 120 and trap 118 and exits through a conduit 122 as suggested by the arrow 124.

When cutting of the plaque accumulation begins in earnest, the debris generated is transported by the irrigating solution through the annulus between the catheter 104 and the artery 94 and then through the catheter 88 to the trap 118. It will accordingly be seen that the technique of this invention is usable at locations near the incision site, as in the embodiment of FIG. 1, and at locations remote from the incision site, as in the embodiment of FIG. 9.

Although this invention has been specifically disclosed in the removal of plaque from a blood vessel, it will be apparent that hard, substantially immobile deposits in other body conduits, such as gall or kidney stones, may be disintegrated by use of the technique of this invention.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A method of removing relatively hard, abnormal deposits from a relatively soft vessel of a patient, comprising
    inserting a catheter into the vessel from a location outside the patient,
    inserting a flexible drive member having first and second ends and a cutting tool on the second end though the catheter and positioning the cutting tool adjacent the deposit, the cutting tool comprising an elongate member defining an axis having a lateral exterior surface extending along the axis and provided with a sharp cutting element; and
    reciprocating the first end of the elongate member at a rate of 3,000–30,000 cycles per minute through a stroke of 0.01–5 millimeters, contacting the hard deposit with the cutting element on the lateral exterior surface and comminuting the hard deposits.

2. A method of removing relatively hard, abnormal deposits from a relatively soft vessel of a patient, comprising
    inserting a catheter into the vessel from a location outside the patient;
    inserting a cutting tool mounted on a flexible drive member through the catheter and positioning the cutting tool adjacent the deposit, the cutting tool comprising an elongate member defining an axis, having a lateral exterior surface extending along the axis and provided with a curvilinear end winding about and spaced from the axis and a sharp cutting element on the curvilinear end, and
    reciprocating the elongate member at a rate of 3,000–30,000 cycles per minute through a stroke of 0.01–5 millimeters by advancing and retracting the curvilinear end of the elongate member through the vessel, contacting the hard deposit with the cutting element on the lateral exterior surface and comminuting the hard deposits.

3. Apparatus for removing relatively hard deposits from a relatively soft vessel of a patient, comprising
    a catheter for placement in the vessel,
    an elongate flexible drive member having a free first end extending into the catheter and a second end;
    a cutting tool on the free end of the flexible drive member having an axis, an exterior surface extending along the axis and a cutting element on the exterior surface;
    means for reciprocating the second end of the flexible drive member through a stroke of 0.01–5 millimeters at a rate of 3,000–30,000 cycles per minute; and
    means for circulating a flushing liquid through the catheter.

4. Apparatus for removing relatively hard deposits from a relatively soft vessel of a patient, comprising
    a catheter for placement in the vessel;
    an elongate flexible drive member having a free end extending into the catheter;
    a cutting tool on the free end of the flexible drive member having an axis, an exterior surface extending along the axis and a cutting element on the exterior surface, the cutting tool comprises an axis and having an exterior surface and a curvilinear end winding about and spaced apart from the axis, the exterior surface being provided with a sharp cutting element;
    means for reciprocating the flexible drive member through a stroke of 0.01–5 millimeters at a rate of 3,000–30,000 cycles per minute; and
    means for circulating a flushing liquid through the catheter.

5. The apparatus of claim 4 wherein the curvilinear end comprises a spiral.

6. The apparatus of claim 4 wherein the curvilinear end comprises a helix.

7. The apparatus of claim 4 wherein the cutting element comprises a helical cutting element extending about the exterior surface of the elongate member.

8. The apparatus of claim 7 wherein the helical cutting element is of triangular cross-section.

9. The apparatus of claim 3 wherein the drive member provides a passage therethrough and the circulating means comprises means for circulating a flushing liquid through the drive member.

10. The apparatus of claim 9 wherein the catheter comprises a balloon seal on the exterior thereof, means for inflating the seal and means for drawing a vacuum on the catheter and further comprising a second catheter, extending through the first mentioned catheter, having therein the flexible drive member and the cutting tool.

11. Apparatus for comminuting a hard body material comprising a catheter and an elongate flexible drive member having a free first end extending into the catheter and a second end; a cutting tool on the free first end of the flexible drive member having an axis, an exterior surface extending along the axis and a cutting element on the exterior surface; means for reciprocating the second end of the flexible drive member through a stroke of 0.01–5 millimeters at a rate of 3,000–30,000 cycles per minute; and means for circulating a flushing liquid through the catheter.

* * * * *